United States Patent
Laurent et al.

(12) 
(10) Patent No.: US 6,673,124 B2
(45) Date of Patent: *Jan. 6, 2004

(54) OXIDATION DYEING PROCESS AND OXIDATION DYE COMPOSITION FOR KERATIN FIBERS WHICH COMPRISES A CATIONIC AMPHIPHILIC POLYMER

(75) Inventors: Florence Laurent, Asnieres (FR); Roland De La Mettrie, Le Vesinet (FR)

(73) Assignee: L'Oreal S.A., Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 207 days.

This patent is subject to a terminal disclaimer.

(21) Appl. No.: 09/263,954

(22) Filed: Mar. 8, 1999

(65) Prior Publication Data

US 2003/0188392 A1 Oct. 9, 2003

(30) Foreign Application Priority Data

Mar. 6, 1998 (FR) .............................................. 98 02775

(51) Int. Cl.$^7$ ................................................ A61K 7/13
(52) U.S. Cl. ...................... 8/406; 8/407; 8/408; 8/435; 8/554; 8/561; 8/562
(58) Field of Search ............................ 8/406, 407, 408, 8/435, 554, 561, 562; 424/70.13

(56) References Cited

U.S. PATENT DOCUMENTS

| | | | |
|---|---|---|---|
| 4,047,888 A | 9/1977 | Papantoniou | 8/411 |
| 4,150,115 A | 4/1979 | Jacquet et al. | 424/70.17 |
| 4,314,807 A * | 2/1982 | Grollier et al. | 8/406 |
| 5,089,257 A | 2/1992 | Schrader et al. | 8/408 |
| 5,288,484 A * | 2/1994 | Tashjian | 424/70.13 |
| 5,376,146 A | 12/1994 | Casperson et al. | |
| 5,393,305 A | 2/1995 | Cohen et al. | |
| 5,685,882 A | 11/1997 | Samain et al. | 8/408 |
| 5,735,908 A * | 4/1998 | Cotteret et al. | 8/410 |
| 5,961,990 A * | 10/1999 | Delrieu et al. | 424/401 |

FOREIGN PATENT DOCUMENTS

| | | |
|---|---|---|
| DE | 2 359 399 | 6/1975 |
| DE | 3 843 892 | 6/1990 |
| DE | 4 133 957 | 4/1993 |
| EP | 0 046 543 | 3/1982 |
| EP | 189935 * | 8/1986 |
| EP | 0503507 | 9/1992 |
| EP | 663203 * | 7/1995 |
| EP | 673641 * | 9/1995 |
| EP | 0 673 641 | 9/1995 |
| EP | 0 763 355 | 3/1997 |
| FR | 1 492 597 | 8/1967 |
| FR | 2 312 233 | 12/1976 |
| FR | 2 331 325 | 6/1977 |
| FR | 2 695 033 | 3/1994 |
| FR | 2 722 684 | 1/1996 |
| GB | 1 026 978 | 4/1966 |
| GB | 1 153 196 | 5/1969 |
| GB | 2 087 180 | 5/1982 |
| GB | 2 096 180 | 10/1982 |
| GB | 2 188 948 | 10/1987 |
| JP | 88-169571 | 7/1988 |
| JP | 91-033495 | 2/1991 |
| JP | 3 294217 | 12/1991 |
| JP | 4 282307 | 10/1992 |
| JP | 7 267832 | 10/1995 |
| JP | 7 309727 | 11/1995 |
| JP | 10 45547 | 2/1998 |
| WO | WO 94/08969 | 4/1994 |
| WO | WO 94/08970 | 4/1994 |

OTHER PUBLICATIONS

English language Abstract of JP 4 282307.
English language Abstract of JP 3 294217.
English language Abstract of JP 7 267832.
English language Abstract of JP 7 309727.
English language Abstract of JP 10 45547.
English language Derwent Abstract of DE 2 369 399, 6/75.
English language Derwent Abstract of DE 3 843 892, 6/90.
English language Derwent Abstract of DE 4 133 957, 4/93.
English language Derwent Abstract of EP 0 673 641, 9/95.
English language Derwent Abstract of FR 2 695 033, 3/94.
English language Derwent Abstract of JP 2019576, 1/90.
English language Derwent Abstract of JP 91–033495, 5/91.

* cited by examiner

Primary Examiner—Margaret Einsmann
(74) Attorney, Agent, or Firm—Finnegan, Henderson, Farabow, Garrett & Dunner, LLP

(57) ABSTRACT

The invention relates to an oxidation dyeing process for human keratin fibers, which comprises applying to the fibers a dye composition (A) containing, in a medium which is suitable for dyeing, at least one oxidation dye precursor and optionally one or more couplers; developing the color in alkaline, neutral or acidic medium using an oxidizing composition (B) containing an oxidizing agent, at least one of the compositions (A) and (B) also containing an effective amount of at least one cationic amphiphilic polymer chosen from quaternized celluloses modified with groups containing at least one fatty chain, chosen from alkyl, arylalkyl and alkylaryl groups containing at least 8 carbon atoms, or mixtures thereof, and quaternized hydroxyethylcelluloses modified with groups containing at least one fatty chain, chosen from alkyl, arylalkyl and alkylaryl groups containing at least 8 carbon atoms, or mixtures thereof; the compositions (A) and (B) being mixed together immediately before use or applied one after the other to the keratin fibers.

45 Claims, No Drawings

OXIDATION DYEING PROCESS AND OXIDATION DYE COMPOSITION FOR KERATIN FIBERS WHICH COMPRISES A CATIONIC AMPHIPHILIC POLYMER

The invention relates to an oxidation dyeing process for keratin fibres, and in particular human keratin fibres such as the hair, with compositions comprising, in a medium which is suitable for dyeing, at least one oxidation dye precursor, optionally one or more couplers, at least one oxidizing agent and at least one cationic amphiphilic polymer.

It is a well known practice to dye keratin fibres, and in particular the hair, with dye compositions containing oxidation dye precursors, which are generally referred to as "oxidation bases", in particular ortho- or para-phenylenediamines, ortho- or para-aminophenols and heterocyclic bases.

Oxidation dye precursors are compounds which are initially colourless or only weakly coloured, and which develop their dyeing power on the hair in the presence of an oxidizing agent. The formation of the coloured compounds results either from a condensation of the "oxidation bases" with themselves or from a condensation of the "oxidation bases" with coloration modifier compounds, or "couplers", which are generally present in the dye compositions used in oxidation dyeing and which are represented more particularly by meta-phenylenediamines, meta-aminophenols and meta-diphenols and certain heterocyclic compounds.

The variety of molecules used, which consist of the "oxidation bases", and of the "couplers", allows a wide variety of colours to be obtained.

During application of the coloration product onto the hair, it is necessary to keep this product on the application area and to prevent it from running onto the face or outside the zones which it is desired to dye. For this, use has been made of traditional thickeners such as crosslinked poly (acrylic acid), hydroxyethylcelluloses, waxes or even certain nonionic surfactants which, when suitably chosen, give rise to a thickening effect, or even a gelling effect, of aqueous media.

However, the inventors have observed that the ingredients of the traditional thickener type, surfactants and solvents, generally halt the rise of the dye on the fibres, which is reflected in less luminous shades. In order to obtain equivalent chromaticity, it is then necessary to use larger amounts of dyes as well as more solvent and/or more surfactants to dissolve these dyes.

The inventors have also found that compositions containing the oxidation dye precursor(s) and, optionally, the coupler(s), and thickened with traditional thickeners, lose some of their gelled nature when they are mixed with the composition containing the oxidizing agent.

After extensive research conducted in this field, the inventors have discovered that introducing an effective amount of a specific cationic associative polymer, as thickener,
  (i) either into the composition containing the oxidation dye precursor(s) and, optionally, the coupler(s) (Composition A),
  (ii) or into the oxidizing composition (Composition B),
  (iii) or into the two compositions (A and B) at the same time,
  gives oxidation dye compositions which, even after mixing with the oxidizing agent, do not run and consequently remain better localized at the point of application. These compositions, moreover, give rise to more chromatic (more luminous) shades and more intense shades than do equivalent compositions containing usual thickener systems.

The colorations obtained moreover have good resistance to perspiration.

For the purposes of the invention, the chromaticity (luminosity) is defined by the value $C^*$ in the $L^*$, $a^*$, $b^*$ colorimetric notation system of the Commission Internationale de l'Éclairage (C.I.E.) [International Commission on Illumination]. This value is equal to the square root of the sum $a^2+b^2$ (+a is red, −a is green, +b is yellow, −b is blue). A shade is proportionately more luminous the larger the value of $C^*$. In this notation system, $L^*$ defines the intensity of the shade. The shade is proportionately more intense the lower the value of $L^*$ (0=black, 100=white).

By means of the invention, it is also possible to advantageously reduce, or even dispense with altogether, the use of surfactants.

The invention also makes it possible to reduce the amount of colouring active materials used in the dye compositions when compared with the conventional and known techniques of the prior art.

According to the invention, the term "associative polymers" means water-soluble polymers capable, in an aqueous medium, of reversibly combining with each other or with other molecules. The chemical structure of these polymers, also known as "amphiphilic polymers", is characterized by the presence of hydrophilic zones which provide the water-solubility, and of hydrophobic zones by which the polymers, in an aqueous medium, assemble with each other or with the hydrophobic parts of other molecules.

One subject of the invention is thus a process for dyeing keratin fibres, and in particular human keratin fibres such as the hair, which comprises applying to the fibres an oxidation dye composition (A) containing, in a medium which is suitable for dyeing, at least one oxidation dye precursor and optionally one or more couplers, and in developing the colour in alkaline, neutral or acidic medium using an oxidizing composition (B) containing an oxidizing agent, at least one of the compositions (A) and (B) also containing an effective amount of at least one cationic amphiphilic polymer chosen from:
  quaternized celluloses modified with groups containing at least one fatty chain selected from alkyl, arylalkyl and alkylaryl groups, preferably containing at least 8 carbon atoms, more preferably 8 to 30 carbon atoms, which, of course, includes mixtures thereof, and
  quaternized hydroxyethylcelluloses modified with groups containing at least one fatty chain selected from alkyl, arylalkyl and alkylaryl groups, preferably containing at least 8 carbon atoms, more preferably 8 to 30 carbon atoms, which, of course, includes mixtures thereof,
  preferably the compositions (A) and (B) being mixed together immediately before use or applied one after the other to the keratin fibres.

Another subject of the invention is also an oxidation dye composition for keratin fibres, in particular for human keratin fibres, which comprises, in a medium which is suitable for dyeing, at least one oxidation dye precursor, where appropriate, one or more couplers and at least one cationic amphiphilic polymer chosen from:
  quaternized celluloses modified with groups containing at least one fatty chain selected from alkyl, arylalkyl and alkylaryl groups, preferably containing at least 8 carbon atoms, which, of course, includes mixtures thereof, and
  quaternized hydroxyethylcelluloses modified with groups containing at least one fatty chain selected from alkyl, arylalkyl and alkylaryl groups, preferably containing at least 8 carbon atoms, which, of course, includes mixtures thereof.

Another subject of the invention is an oxidizing composition which is used to develop the colour of an oxidation dye composition and comprising at least one oxidizing agent and at least one cationic amphiphilic polymer as defined above.

Yet another subject of the invention is a ready-to-use composition for dyeing keratin fibres, which contains at least one oxidation dye precursor, optionally one or more couplers, at least one cationic amphiphilic polymer as defined above and at least one oxidizing agent.

Another subject of the invention includes multi-compartment dyeing devices or dyeing kits containing at least two compartments, one of which contains a composition (A) comprising, in a medium which is suitable for dyeing, at least one oxidation dye precursor and optionally one or more couplers, and another compartment contains an oxidizing composition (B) comprising at least one oxidizing agent, at least one of the compositions (A) and (B) also comprising an effective amount of at least one cationic amphiphilic polymer as defined above.

The alkyl radicals borne by the above quaternized celluloses or hydroxyethylcelluloses preferably contain from 8 to 30 carbon atoms, more preferably 12 to 18 carbon atoms. The aryl radicals are preferably phenyl, benzyl, naphthyl or anthryl groups.

Representative quaternized alkylhydroxyethylcelluloses containing $C_{8-30}$ fatty chains include the products Quatrisoft LM 200, Quatrisoft LM-X-529-18-A, Quatrisoft LM-X-529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

The cationic amphiphilic polymers used in the compositions of the present invention are preferably present in an amount ranging from 0.05 to 10% by weight, more preferably in an amount ranging from 0.1 to 5% by weight, even more preferably from 0.1 to 0.2%, relative to the weight of the oxidation dye composition (A) or of the oxidizing composition (B).

The oxidation dye precursors which can be used in the context of the present invention are chosen from those conventionally known in oxidation dyeing. Representative oxidation dye precursors include:

the para-phenylenediamines of formula (I) below, and the acid addition salts thereof

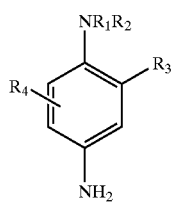

(I)

in which
$R_1$ represents a hydrogen atom or a $C_{1-4}$ alkyl radical, a $C_{1-4}$ monohydroxyalkyl radical, a $C_{2-4}$ polyhydroxyalkyl radical or a 4'-aminophenyl radical,
$R_2$ represents a hydrogen atom or a $C_{1-4}$ alkyl radical, a $C_{1-4}$ monohydroxyalkyl radical or a $C_{2-4}$ polyhydroxyalkyl radical,
$R_3$ represents a hydrogen atom, a halogen atom such as a chlorine atom, or a $C_{1-4}$ alkyl radical, a sulpho radical, a carboxyl radical, a $C_{1-4}$ monohydroxyalkyl radical or a $C_{1-4}$ hydroxyalkoxy radical,
$R_4$ represents a hydrogen atom or a $C_{1-4}$ alkyl radical.

Preferred para-phenylenediamines of formula (I) above are, for example para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para- phenylenediamine, 2,5-dimethyl-para-phenylenediamine, N,N-dimethyl-para-phenylenediamine, N,N-diethyl-para-phenylenediamine, N,N-dipropyl-para-phenylene-diamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl) aniline, 2-β-hydroxyethyl-para-phenylenediamine, 2-fluoro-para-phenylenediamine, 2-isopropyl-para-phenylene, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the acid addition salts thereof.

Among the para-phenylenediamines of formula (I) above, the ones most particularly preferred are para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine and 2-chloro-para-phenylenediamine, and the acid addition salts thereof.

the bis(phenyl)alkylenediamines of formula (II):

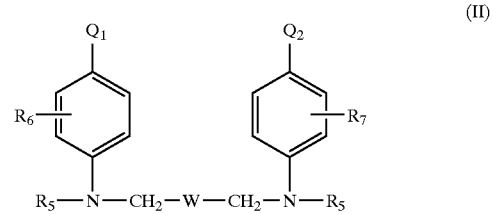

(II)

in which
$Q_1$ and $Q_2$, which may be identical or different, represent a hydroxyl radical or a $NHR_8$ radical in which $R_8$ represents a hydrogen atom or a $C_{1-4}$ alkyl radical,
$R_5$ represents a hydrogen atom or a $C_{1-4}$ alkyl radical, a $C_{1-4}$ monohydroxyalkyl radical, a $C_{2-4}$ polyhydroxyalkyl radical or a $C_{1-4}$ aminoalkyl radical in which the amino group may be substituted,
$R_6$ and $R_7$, which may be identical or different, represent a hydrogen or a halogen atom or a $C_{1-4}$ alkyl radical,
W represents a radical chosen from the group formed by the following radicals:
—$(CH_2)_n$—; —$(CH_2)_m$—O—$(CH_2)_m$; —$(CH_2)_m$—CHOH—$(CH_2)_m$— and
—$(CH_2)_m$—N($CH_3$)—$(CH_2)_m$—;
in which n is an integer from 0 to 8 and m is an integer from 0 to 4, and the acid addition salts thereof.

Representative bis(phenyl)alkylenediamines of formula (II) above include N,N'-bis(β-hydroxyethyl)-N,N'-bis(4- aminophenyl)-1,3-diamino-2-propanol, N,N'-bis(β-hydroxyethyl)-N,N'-bis(4-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetra-methylenediamine, N,N'-bis(β-hydroxy-ethyl)-N,N'-bis(4-aminophenyl)tetramethylenediamine and N,N'-bis(ethyl)-N,N'-bis(4-amino-3-methylphenyl)ethylenediamine, and the acid addition salts thereof.

A preferred bis(phenyl)alkylenediamine of formula (II) is N,N'-bis(β-hydroxyethyl)-N,N'-bis(4'-aminophenyl)-1,3-diamino-2-propanol, or one of the acid addition salts thereof.

the para-aminophenols corresponding to formula (III):

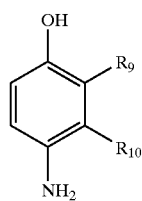

(III)

in which $R_9$ represents a hydrogen atom or a $C_{1-4}$ alkyl radical, a $C_{1-4}$ monohydroxyalkyl radical, a $(C_{1-4})$alkoxy $(C_{1-4})$alkyl radical or a $C_{1-4}$ aminoalkyl radical , or a hydroxy$(C_{1-4})$alkylamino$(C_{1-4})$alkyl radical;

$R_{10}$ represents a hydrogen or fluorine atom or a $C_{1-4}$ alkyl radical, a $C_{1-4}$ monohydroxyalkyl radical, a $C_{2-4}$ polyhydroxyalkyl radical, a $C_{1-4}$ aminoalkyl radical, a cyano$(C_{1-4})$alkyl radical or a $(C_{1-4})$alkoxy $(C_{1-4})$alkyl radical, and the acid addition salts thereof, with the proviso that at least one of the radicals $R_9$ or $R_{10}$ represents a hydrogen atom.

Preferred para-aminophenols of formula (III) above include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxy-methylphenol, 4-amino-2-aminomethylphenol and 4-amino-2-(β-hydroxyethylaminomethyl)phenol, and the acid addition salts thereof.

the ortho-aminophenols which can be used as oxidation bases in the context of the invention are chosen in particular from 2-aminophenol, 2-amino-1-hydroxy-5-methylbenzene, 2-amino-1-hydroxy-6-methylbenzene and 5-acetamido-2-aminophenol, and the acid addition salts thereof;

the heterocyclic bases which can be used as oxidation bases in the context of the invention are chosen in particular from pyridine derivatives, pyrimidine derivatives and pyrazole derivatives, and the acid addition salts thereof.

Preferred pyridine derivatives include the compounds described, for example, in patents GB-1,026,978 and GB-1,153,196, specifically incorporated by reference herein, such as 2,5-diaminopyridine, and the acid addition salts thereof.

Preferred pyrimidine derivatives include the compounds described, for example, in German patent DE-2,359,399 or Japanese patents JP-88-169,571 and JP-91-333,495, specifically incorporated by reference herein, such as 2,4,5,6-tetraaminopyrimidine and 4-hydroxy-2,5,6-triaminopyrimidine, and the acid addition salts thereof.

Preferred pyrazole derivatives include the compounds described in patents DE-3,843,892, DE-4,133,957 and patent applications WO-94/08969 and WO-94/08970, specifically incorporated by reference herein, such as 4,5-diamino-1-methylpyrazole, 3,4-diaminopyrazole and 4,5-diamino-1-(4'-chlorobenzyl)pyrazole, and the acid addition salts thereof.

According to the invention, the oxidation dye precursor(s) preferably is present in an amount ranging from 0.0005 to 12% by weight relative to the total weight of the composition (A) and more preferably from 0.005 to 6% by weight of the total weight of the composition approximately.

The couplers which can be used in the dyeing process according to the invention are those conventionally used in oxidation dye compositions, i.e. meta-phenylenediamines, meta-aminophenols and meta-diphenols (resorcinols), mono- or polyhydroxylated naphthalene derivatives, sesamol and its derivatives and heterocyclic compounds such as, for example, indole couplers, indoline couplers and pyridine couplers, and the acid addition salts thereof.

These couplers may be chosen in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 1-(β-hydroxyethoxy)-2,4-diaminobenzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one and 1-phenyl-3-methylpyrazol-5-one, and the acid addition salts thereof.

When they are present, these couplers preferably are represent in an amount ranging from about 0.0001 to about 10% by weight relative to the total weight of the composition (A), and in particular from about 0.005 to about 5% by weight of the composition (A).

In general, the acid addition salts thereof the chromogenic compounds, i.e. the oxidation bases and the couplers, are chosen in particular from the hydrochlorides, hydrobromides, sulphates, tartrates, lactates and acetates.

In addition to the oxidation dye precursors defined above and the optional associated couplers, the composition (A) may contain direct dyes in order to enrich the shades with glints. These direct dyes may be chosen in particular from nitro dyes, azo dyes and anthraquinone dyes.

The composition (A) and/or the composition (B) may also contain at least one cationic or amphoteric substantive polymer such as those defined in EP-A-0,673,641, specifically incorporated by reference herein, among which it is advantageously preferred to use:

the poly(quaternary ammonium) polymers prepared and described in French patent 2,270,846, specifically incorporated by reference herein, containing repeating units corresponding to formula (IV) below:

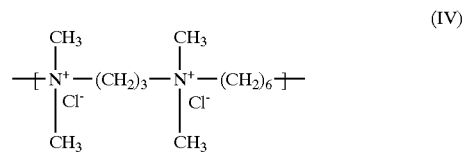

(IV)

and particularly those whose weight-average molar mass, determined by gel permeation chromatography, is from 9500 to 9900;

the poly(quaternary ammonium) polymers prepared and described in French patent 2,270,846, specifically incorporated by reference herein, containing repeating units corresponding to formula (V) below:

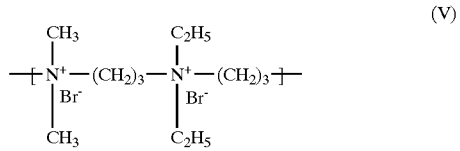

and particularly those whose weight-average molar mass, determined by gel permeation chromatography, is about 1200.

The medium for the composition (A) which is suitable for dyeing is preferably an aqueous medium consisting mainly of water and optionally containing cosmetically acceptable organic solvents, among which are alcohols such as ethyl alcohol, isopropyl alcohol, benzyl alcohol and phenylethyl alcohol; glycols or glycol ethers such as ethylene glycol monomethyl, monoethyl and monobutyl ethers, propylene glycol or its ethers, such as propylene glycol monomethyl ether; butylene glycol; dipropylene glycol and diethylene glycol alkyl ethers such as, for example, diethylene glycol monomethyl or monobutyl ether, in concentrations ranging from about 0.5 to about 20% by weight, and preferably from about 2 to about 10% by weight, relative to the total weight of the composition.

The composition (A) and/or the composition (B) may also contain an effective amount of other agents commonly used in the cosmetics field. These adjuvants are, for example, sequestering agents, hair conditioners and in particular silicones, preserving agents, opacifiers, etc., and optionally anionic, nonionic or amphoteric surfactants, or mixtures thereof.

The said dye composition may also contain antioxidants. These can be chosen in particular from sodium sulphite, thioglycolic acid, thiolactic acid, sodium bisulphite, dehydroascorbic acid, hydroquinone, 2-methylhydroquinone, tert-butylhydroquinone and homogentisic acid. They are present, where appropriate, in an amount ranging from about 0.05 to about 3.0% by weight relative to the total weight of the composition.

Needless to say, a person skilled in the art will take care to select the optional complementary compound(s) mentioned above, such that the advantageous properties intrinsically associated with the dye composition according to the invention are not, or are virtually not, adversely affected by the addition(s) envisaged.

In the composition (B), the oxidizing agent is preferably chosen from hydrogen peroxide, urea peroxide, alkali metal bromates or ferricyanides, and salts of peracids such as perborates, percarbonates and persulphates. It is preferred in particular to use hydrogen peroxide.

The composition (B) advantageously comprises an aqueous hydrogen peroxide solution whose titre preferably ranges from about 2.5 to about 40 volumes, in particular from about 5 to about 20 volumes.

The value of the pH of the ready-to-use composition, resulting from mixing the dye composition (A) and the oxidizing composition (B), generally ranges from 4 to 11, and preferably from 6 to 10.5. It can be adjusted using acidifying or basifying agents which are well known in the art of oxidation dyeing of keratin fibres.

Among the basifying agents which may be used, for example, are aqueous ammonia, alkali metal carbonates, alkanolamines such as mono-, di- and triethanolamine and derivatives thereof, sodium hydroxide, potassium hydroxide and the compounds of formula (VI) below:

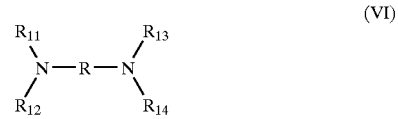

in which R is a propylene residue optionally substituted with a hydroxyl group or a $C_{1-4}$ alkyl radical; $R_{11}$, $R_{12}$, $R_{13}$ and $R_{14}$, which may be identical or different, represent a hydrogen atom or a $C_{1-4}$ alkyl radical or a $C_{1-4}$ hydroxyalkyl radical.

The acidifying agents are conventionally, for example, inorganic or organic acids such as hydrochloric acid, orthophosphoric acid, carboxylic acids such as tartaric acid, citric acid or lactic acid, or sulphonic acids.

The dyeing process according to the invention preferably comprises applying a mixture, prepared extemporaneously at the time of use from the compositions (A) and (B) described above, to the wet or dry keratin fibres, and in leaving this mixture to act for an exposure time preferably ranging from 1 to 60 minutes approximately, and more particularly from 10 to 45 minutes approximately, rinsing the fibres, then optionally washing them with shampoo and rinsing them again and drying them.

It is clearly understood that the preceding description has been given purely for non-limiting illustrative purposes and that variants or modifications may be made thereto in the context of the present invention.

Examples illustrating the invention will now be given, without, however, being limiting in nature.

EXAMPLE

The following oxidation dye composition is prepared:

| | |
|---|---|
| oxyethylenated (3) decyl alcohol | 9% |
| oleyl alcohol | 6% |
| oleic acid | 3% |
| alkylpolyglycoside (1.4) | 6.9% |
| ethyl alcohol | 6.5% |
| ethylene glycol monobutyl ether | 10% |
| quaternized laurylhydroxyethylcellulose (sold under the name Quatrisoft LM 200 by the company Amerchol) | 0.2% |
| sequestering agent | qs |
| reducing agent | qs |
| fragrance | qs |
| antioxidant | qs |
| 20% aqueous ammonia | 10% |
| 1,3-dihydroxybenzene | 0.4% |
| 3-aminophenol | 0.074% |
| 1-(β-hydroxyethoxy)-2,4-diaminobenzene dihydrochloride | 0.0094% |
| 1,3-dihydroxy-2-methylbenzene | 0.15% |
| N,N'-bis(β-hydroxyethyl)-N,N'-bis-(4-aminophenyl)-1,3-diamino-2-propanol tetrahydrochloride | 0.1% |
| para-phenylenediamine | 0.63% |
| demineralized water | qs 100% |

The above dye composition is mixed, at the time of use, weight for weight with a 20-volumes hydrogen peroxide solution (6% by weight).

The mixture obtained is applied to locks of natural grey hair containing 90% white hairs, for 30 minutes. The locks are then rinsed, washed with a standard shampoo, rinsed again and then dried.

A light-chestnut shade is obtained.

What is claimed is:

1. An oxidation dye composition for keratin fibers wherein said composition comprises, in a medium which is suitable for dyeing, at least one oxidation dye precursor and at least one cationic amphiphilic polymer,
wherein said at least one oxidation dye precursor is chosen from:
ortho-phenylenediamines,
para-phenylenediamines of formula (I)

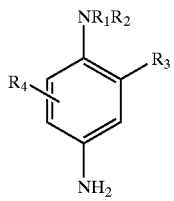

in which
$R_1$ represents a hydrogen atom or a $C_{1-4}$ alkyl radical, a $C_{1-4}$ monohydroxyalkyl radical, a $C_{2-4}$ polyhydroxyalkyl radical or a 4'-aminophenyl radical,
$R_2$ represents a hydrogen atom or a $C_{1-4}$ alkyl radical, a $C_{1-4}$ monohydroxyalkyl radical or a $C_{2-4}$ polyhydroxyalkyl radical,
$R_3$ represents a hydrogen atom, a halogen atom, or a $C_{1-4}$ alkyl radical, a sulpho radical or a carboxyl radical,
$R_4$ represents a hydrogen atom or a $C_{1-4}$ alkyl radical,
bis(phenyl)alkylenediamines,
ortho- and para- aminophenols,
heterocyclic bases and the acid addition salts thereof,
and said at least one cationic amphiphilic polymer is chosen from quaternized celluloses modified with groups containing at least one fatty chain, selected from alkyl, arylalkyl and alkylaryl groups containing from 8 to 30 carbon atoms, said quaternized celluloses including hydroxyethylcelluloses.

2. The composition according to claim 1, further comprising at least one coupler.

3. The composition according to claim 2, wherein said at least one coupler is chosen from meta-phenylenediamines, meta-aminophenols, meta-diphenols, heterocyclic couplers, and the acid addition salts thereof.

4. The composition according to claim 3, wherein said acid addition salts are selected from the hydrochlorides, hydrobromides, sulphates, tartrates, lactates and acetates.

5. The composition according to claim 2 wherein said at least one coupler is present in an amount ranging from 0.0001 to 10% by weight relative to the total weight of the composition.

6. The composition according to claim 5, wherein said at least one coupler is present in an amount ranging from 0.005 to 5%.

7. The composition according to claim 1, wherein said medium suitable for dyeing is an aqueous medium comprising water and optionally containing at least one cosmetically acceptable organic solvent.

8. The composition according to claim 7, wherein said at least one organic solvent is selected from ethyl alcohol, isopropyl alcohol, benzyl alcohol, phenylethyl alcohol, glycols, and glycol ethers.

9. The composition according to claim 8, wherein said glycols are selected from butylene glycol and dipropylene glycol and said glycol ethers are selected from diethylene glycol alkyl ethers.

10. The composition according to claim 1, wherein said alkyl groups containing from 8 to 30 carbon atoms are selected from $C_{12}$ and $C_{18}$ alkyl groups.

11. The composition according to claim 10, wherein said alkyl groups containing $C_{12}$ to $C_{18}$ alkyl groups are $C_{12}$ alkyl groups.

12. The composition according to claim 1, wherein said composition additionally contains direct dyes.

13. The composition according to claim 1, wherein said composition additionally contains at least one adjuvant selected from sequestering agents, hair conditioners, preserving agents, opacifiers and anionic, nonionic and amphoteric surfactants.

14. The composition according to claim 13, wherein said hair conditioners are silicones.

15. The composition according to claim 1, wherein said composition additionally contains at least one antioxidant in an amount ranging from 0.05 to 3% by weight relative to the total weight of the composition.

16. The composition according to claim 1, wherein said composition further comprises at least one cationic or amphoteric substantive polymer which is a poly(quaternary ammonium) polymer containing repeating units corresponding to formula (IV) below:

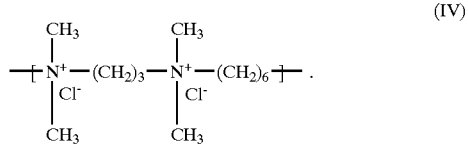

17. The composition according to claim 1, wherein said composition further comprises at least one cationic or amphoteric substantive polymer which is a poly(quaternary ammonium) polymer containing repeating units corresponding to formula (V) below:

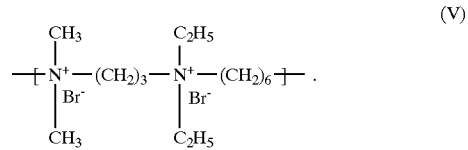

18. The composition according to claim 1, wherein said acid addition salts are chosen from hydrochlorides, hydrobromides, sulphates, tartrates, lactates and acetates.

19. The composition according to claim 1, wherein said oxidation dye precursors are present in an amount ranging from 0.0005 to 12% by weight relative to the total weight of the composition.

20. The composition according to claim 1, wherein said at least one cationic amphiphilic polymer is present in an amount ranging from 0.05 to 10% by weight of the oxidation dye composition.

21. The composition according to claim 20, wherein said at least one cationic amphiphilic polymer is present in an amount ranging from 0.1 to 5%.

22. The composition according to claim 19, wherein said oxidation dye precursors are present in an amount ranging from 0.005 to 6%.

23. A ready-to-use composition for dyeing keratin fibers comprising at least one oxidation dye precursor, at least one oxidizing agent, and at least one cationic amphiphilic polymer,
   wherein said at least one oxidation dye precursor is chosen from:
   ortho-phenylenediamines,

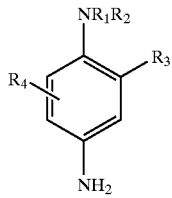

(I)

para-phenylenediamines of formula (I)
      in which
         $R_1$ represents a hydrogen atom or a $C_{1-4}$ alkyl radical, a $C_{1-4}$ monohydroxyalkyl radical, a $C_{2-4}$ polyhydroxyalkyl radical or a 4'-aminophenyl radical,
         $R_2$ represents a hydrogen atom or a $C_{1-4}$ alkyl radical, a $C_{1-4}$ monohydroxyalkyl radical or a $C_{2-4}$ polyhydroxyalkyl radical,
         $R_3$ represents a hydrogen atom, a halogen atom, or a $C_{1-4}$ alkyl radical, a sulpho radical or a carboxyl radical,
         $R_4$ represents a hydrogen atom or a $C_{1-4}$ alkyl radical,
      bis(phenyl)alkylenediamines,
      ortho- and para- aminophenols,
      heterocyclic bases and the acid addition salts thereof,
   and said at least one cationic amphiphilic polymer is chosen from quaternized celluloses modified with groups containing at least one fatty chain, selected from alkyl, arylalkyl and alkylaryl groups containing from 8 to 30 carbon atoms, said quaternized celluloses including hydroxyethylcelluloses.

24. The composition according to claim 23 further comprising at least one coupler.

25. The composition according to claim 24, wherein said at least one coupler is chosen from meta-phenylenediamines, meta-aminophenols, meta-diphenols, heterocyclic couplers, and the acid addition salts thereof.

26. The composition according to claim 24 wherein said at least one coupler is present in an amount ranging from 0.0001 to 10% by weight relative to the total weight of the composition.

27. The composition according to claim 23, wherein said at least one cationic amphiphilic polymer is present in an amount ranging from 0.05 to 10% by weight of the ready-to-use composition.

28. The composition according to claim 26, wherein said at least one coupler is present in an amount ranging from 0.005 to 5%.

29. The composition according to claim 23, wherein said oxidation dye precursors are present in an amount ranging from 0.0005 to 12% by weight relative to the total weight of the composition.

30. The composition according to claim 29, wherein said oxidation dye precursors are present in an amount ranging from 0.005 to 6%.

31. The composition according to claim 27, wherein said at least one cationic amphiphilic polymer is present in an amount ranging from 0.1 to 5%.

32. The composition according to claim 23, wherein said acid addition salts are chosen from hydrochlorides, hydrobromides, sulphates, tartrates, lactates and acetates.

33. The composition according to claim 23, wherein said composition has a pH ranging from 4 to 11.

34. The composition according to claim 33, wherein said composition has a pH ranging from 6 to 10.5.

35. The composition according to claim 23, wherein said oxidizing agent is selected from hydrogen peroxide, urea peroxide, alkali metal bromates, ferricyanides, and salts of peracids.

36. The composition according to claim 23, wherein said oxidizing agent is an aqueous hydrogen peroxide solution whose titre ranges from 2.5 to 40 volumes.

37. The composition according to claim 36, wherein said oxidizing agent is an aqueous hydrogen peroxide solution whose titre ranges from 5 to 20 volumes.

38. The composition according to claim 23, wherein said alkyl groups containing from 8 to 30 carbon atoms are selected from $C_{12}$ and $C_{18}$ alkyl groups.

39. The composition according to claim 38, wherein said alkyl groups containing $C_{12}$ to $C_{18}$ alkyl groups are $C_{12}$ alkyl groups.

40. The composition according to claim 23, wherein said composition additionally contains direct dyes.

41. The composition according to claim 25, wherein said acid addition salts are selected from the hydrochlorides, hydrobromides, sulphates, tartrates, lactates and acetates.

42. A process for dyeing keratin fibers comprising:
   applying to said fibers an oxidation dye composition (A) containing in a medium which is suitable for dyeing, at least one oxidation dye precursor, and
   developing a color in alkaline, neutral or acidic medium by applying to said fibers an oxidizing composition (B) containing an oxidizing agent, at least one of the compositions (A) and (B) also containing an effective amount of at least one cationic amphiphilic polymer,
   wherein said at least one oxidation dye precursor is chosen from:
   ortho-phenylenediamines,
   para-phenylenediamines of formula (I)

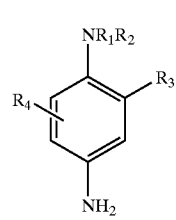

(I)

in which
      $R_1$ represents a hydrogen atom or a $C_{1-4}$ alkyl radical, a $C_{1-4}$ monohydroxyalkyl radical, a $C_{2-4}$ polyhydroxyalkyl radical or a 4'-aminophenyl radical,
      $R_2$ represents a hydrogen atom or a $C_{1-4}$ alkyl radical, a $C_{1-4}$ monohydroxyalkyl radical or a $C_{2-4}$ polyhydroxyalkyl radical,
      $R_3$ represents a hydrogen atom, a halogen atom, or a $C_{1-4}$ alkyl radical, a sulpho radical or a carboxyl radical,
      $R_4$ represents a hydrogen atom or a $C_{1-4}$ alkyl radical,
   bis(phenyl)alkylenediamines,
   ortho- and para- aminophenols, heterocyclic bases and the acid addition salts thereof, and said at least one cationic amphiphilic polymer is chosen from quaternized celluloses modified with groups containing at least one fatty chain, selected from alkyl, arylalkyl and alkylaryl groups containing from 8 to 30 carbon atoms, wherein said compositions (A) and (B) are mixed together immediately before being applied to said keratin fibers or wherein said compositions (A) and (B) are applied one after the other to the keratin fibers.

43. The process according to claim 42, wherein said keratin fibres are human keratin fibres.

44. The process according to claim 43, wherein said human keratin fibres are hair.

45. A multi-compartment device or kit for dyeing keratin fibers wherein said device or kit comprises at least two compartments, one of which contains an oxidation dye composition (A) comprising in a medium which is suitable for dyeing, at least one oxidation dye precursor and another compartment contains an oxidizing composition (B) comprising at least one oxidizing agent, wherein at least one of the compositions (A) and (B) also contains an effective amount of at least one cationic amphiphilic polymer, wherein said at least one oxidation dye precursor is chosen from:

ortho-phenylenediamines, para-phenylenediamines of formula (I)

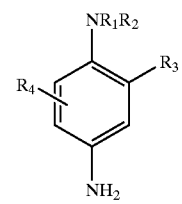

in which
$R_1$ represents a hydrogen atom or a $C_{1-4}$ alkyl radical, a $C_{1-4}$ monohydroxyalkyl radical, a $C_{2-4}$ polyhydroxyalkyl radical or a 4'-aminophenyl radical,
$R_2$ represents a hydrogen atom or a $C_{1-4}$ alkyl radical, a $C_{1-4}$ monohydroxyalkyl radical or a $C_{2-4}$ polyhydroxyalkyl radical,
$R_3$ represents a hydrogen atom, a halogen atom, or a $C_{1-4}$ alkyl radical, a sulpho radical or a carboxyl radical,
$R_4$ represents a hydrogen atom or a $C_{1-4}$ alkyl radical,
bis(phenyl)alkylenediamines,
ortho- and para- aminophenols,
heterocyclic bases and the acid addition salts thereof,
and said at least one cationic amphiphilic polymer is chosen from quaternized celluloses modified with groups containing at least one fatty chain, selected from alkyl, arylalkyl and alkylaryl groups containing from 8 to 30 carbon atoms, said quaternized celluloses including hydroxyethylcelluloses.

* * * * *

UNITED STATES PATENT AND TRADEMARK OFFICE
CERTIFICATE OF CORRECTION

PATENT NO.   : 6,673,124 B2
DATED        : January 6, 2004
INVENTOR(S)  : Florence Laurent et al.

It is certified that error appears in the above-identified patent and that said Letters Patent is hereby corrected as shown below:

Title page,
Item [*] Notice, "Subject to any disclaimer, the term of this patent is extended or adjusted under 35 U.S.C. 154(b) by 207 days," should read -- Subject to any disclaimer, the term of this patent is extended or adjusted under 35 U.S.C. 154(b) by 0 days. --.

Signed and Sealed this

Thirteenth Day of September, 2005

JON W. DUDAS
*Director of the United States Patent and Trademark Office*